United States Patent [19]

Albrecht et al.

[11] 4,217,304
[45] Aug. 12, 1980

[54] CONTINUOUS REDUCTION PROCESS

[75] Inventors: Bernhard Albrecht, Buus; Hans Frey, Bettingen; Vinzenz Habermacher, Basel; Paul Havalda, Arlesheim, all of Switzerland; Georg Halfter, Wyhlen, Fed. Rep. of Germany

[73] Assignee: Ciba-Geigy AG, Basel, Switzerland

[21] Appl. No.: 971,276

[22] Filed: Dec. 20, 1978

[30] Foreign Application Priority Data

Dec. 23, 1977 [CH] Switzerland ............... 15960/77

[51] Int. Cl.$^2$ ............... C07C 85/11; C07C 143/58; C07C 143/60; C07C 143/62
[52] U.S. Cl. ............... 260/508; 260/509; 260/510; 260/580; 260/378; 548/363; 562/433; 562/456
[58] Field of Search ............... 260/508, 510, 580, 378, 260/509; 548/363; 562/433, 456

[56] References Cited

U.S. PATENT DOCUMENTS

| 2,405,137 | 8/1946 | Gale et al. | 260/580 |
| 2,619,503 | 11/1952 | Benner et al. | 260/580 |
| 3,517,063 | 6/1970 | Nason | 260/580 |
| 3,761,521 | 9/1973 | Alheritiere et al. | 260/580 |

FOREIGN PATENT DOCUMENTS 1520343  8/1978  United Kingdom ............... 260/508

OTHER PUBLICATIONS

Kirk–Othmer, Encyclopedia of Chemical Technology, 2nd edition, vol. 2, pp. 83-91, 1963.

Primary Examiner—Nicky Chan
Attorney, Agent, or Firm—Sprung, Felfe, Horn, Lynch & Kramer

[57] ABSTRACT

A process for the reduction of aromatic nitro compounds to amino compounds in the liquid phase using iron as reducing agent, which comprises carrying out the reduction continuously such that the reducing iron, based on the amount of nitro compound present in the reactor, is present in an amount substantially in excess of the stoichiometric amount, and effecting the continuous removal of the reaction products such that the substantial excess of reducing iron is also constantly present in the reactor during the reduction.

18 Claims, 1 Drawing Figure

U.S. Patent          Aug. 12, 1980          4,217,304
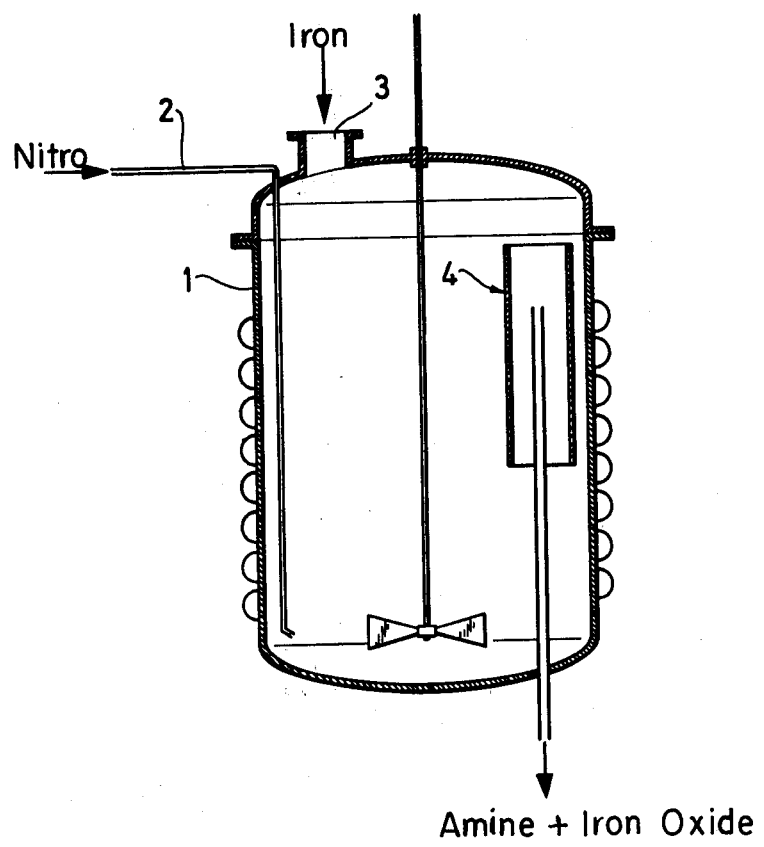

CONTINUOUS REDUCTION PROCESS

The present invention concerns a continuous process for the reduction of aromatic nitro compounds to amino compounds using iron as reducing agent.

The reduction process is in itself known in chemical process technology by the name of Béchamp reduction and ranks as one of the conventional methods. In recent times, this reduction method has been increasingly displaced by other methods, especially reduction with hydrogen, as increasing amounts of inexpensive hydrogen are obtained in petrochemical and electrolysis installations. The development of catalytic methods of hydrogenating, for example, aromatic nitro compounds has been thereby facilitated, especially as these methods require relatively low investment costs. A drawback in the reduction with hydrogen is, however, the need for expensive heavy metal, and in particular, noble metal, catalysts.

These new reduction methods have also been able to gain acceptance because the batchwise operated Béchamp reduction, apart from the iron oxide obtained, is encumbered with drawbacks. The removal of waste, sieving and grinding as well as the agitation of the total amount of iron turnings required is work-intensive and can only be accomplished by employing complicated apparatus. In addition, losses of iron and end product occur in the working up of the products in the batchwise method, as the oxidation of the iron is not complete.

It has now been found that the reduction with iron can also be carried out continuously employing a corresponding apparatus assembly. The drawbacks of the batchwise method referred to above are thereby eliminated.

Accordingly, the invention provided a process for the reduction of aromatic nitro compounds to amino compounds in the liquid phase using iron as reducing agent, which comprises carrying out the reduction continuously such that the reducing iron, based on the amount of nitro compound present in the reactor, is present in an amount substantially in excess of the stoichiometric amount, and effecting the continuous removal of the reaction products such that the substantial excess of reducing iron is also constantly present in the reactor during the reduction.

The possibility of carrying out the process continuously has been afforded by making changes in the reduction apparatus.

The sole FIGURE in this case is a schematic view of a steel reactor apparatus for carrying out the process of the present invention.

The principle feature of the invention resides in the continuous removal of the reaction products and the subsequent separation of the aromatic amine from the iron oxide simultaneously formed. The continuous removal of the reaction products from the reduction apparatus can be accomplished in different ways, for example via a suitable overflow, or by means of a separating unit with overflow outside the reactor, in which the resulting amine, together with the iron oxide and any entrained iron powder, flows or is pumped into a settling tank from which the deposited iron is recycled to the reduction assembly and the overflow from this vessel consists of the amine which is dissolved or suspended in the reaction medium and iron oxide sludge.

An apparatus assembly as illustrated in the attached drawing is particularly advantageous. A separation of iron oxide from any iron particles is effected by means of the overflow and the iron separator. Amine and iron oxide are removed continuously from the reaction through the overflow pipe. The degree of separation is controlled by the reaction rate, and consequently by the construction of the reduction apparatus, in respect of the reaction volume.

The reaction is suitable in particular for the reduction of nitro compounds which are dissolved in the reaction medium. However, it can also be used for suspensions. The preferred reaction medium is water; but other dissolving or dispersing media are also possible. Exemplary thereof are polar solvents which are inert to the reduction under the given conditions.

The aromatic nitro compounds to be reduced can be liquid or solid. They can contain one or more nitro groups which undergo reduction. In addition, they can also contain other substituents, for example sulfo groups, halogen atoms, hydroxyl, alkyl, alkoxy, acylamino, carboxamido, sulfonamide or alkylsulfone groups.

Preferred nitro compounds are those of the phenyl or naphthyl series; but other aromatic compounds are also eligible.

As examples there may be mentioned:
nitrobenzene,
2-nitrobenzenesulfonic acid,
2-nitrobenzoic acid,
2,6-dinitrotoluene,
1,4-dinitro-2,5-dichlorobenzene,
3-nitro-4-chlorobenzoic acid,
1-nitrobenzene-2-sulfocyclohexylamide,
4-acetamino-2-nitrophenol-6-sulfonic acid,
2-nitro-4-(1)-amylphenol-6-sulfonic acid,
4-nitro-3'-chloro-stilbene-2-sulfonic acid,
2-nitro-4'-methyl-diphenylsulfone-4-sulfonic acid,
2,5-dinitro-4'-methyl-diphenylsulfone,
4,4'-dinitrostilbene-2,2'-disulfonic acid,
2-nitro-4-methylsulfonylphenol,
2-nitro-2'-sulfo-4,4'-dichlorodiphenyl ether,
nitrobenzenedisulfonic acid-2,5,
meta-nitrobenzenesulfonic acid,
3-nitro-4-hydroxyphenyl-methylsulfone,
1-nitronaphthalene,
5,8-dichloro-1-nitronaphthalene,
2-nitro-6-naphthol-8-sulfonic acid,
2-(4-nitrobenzamido)-6-naphthol-8-sulfonic acid,
1-(3-nitrobenzamido)-8-naphthol-3,6- or -4,6-disulfonic acid
1-(4'-nitrophenyl)-3-methyl-pyrazolone-(5),
1-nitroanthraquinone,
and especially nitronaphthalenesulfonic acid, such as nitroperi acid, nitro-laurent acid and nitro-C acid.

The reduction is carried out in a weakly acid to weakly alkaline reaction medium and the pH can be in the range between 4 and 10. Preferably, however, the reduction is carried out in the pH range between 5.5 and 8.5, whilst the choice of the pH value within this range often depends on the better solubility of the reaction substrate or product.

The reaction temperature is advantageously in the range between 70° and 130° C., in particular, however, between 90° and 110° C. On account of the weak solution of heat, the reaction is self-supporting as regards the energy requirement. Energy need only be applied to initiate the reaction.

The iron used as reducing agent is advantageously employed in powder form or in the form of fine turnings. In particular it is carbonaceous iron, for example cast-iron or normal carbon-containing iron having a particle size distribution of up to 10 mm, advantageously up to 0.5 mm. In particular, the untreated cast-iron turnings which occur, for example, in the machining of work pieces are used.

The amount of iron required is 2.25 moles per mole of nitro group to be reduced. In this connection, it is advantageous to employ an excess of 20% of this amount. The iron does not need to be activated by the addition of acids or salts, as is necessary in the process disclosed in German Offenlegungsschrift No. 2,534,176. Usually the reaction commences of its own accord, depending on the pH value. It is also possible to use other metals, for example zinc, as reducing agent. However, iron is preferred for commercial reasons.

The reduction process of the present invention proceeds as follows:

The nitro compound to be reduced is dissolved in as high a concentration as possible in the reaction medium, usually in water. The concentration is usually in the range of about 30%. The reduction assembly 1 of the attached drawing is charged with a requisite amount of the reducing iron, namely 150 to 500 g of iron per mole of nitro group to be reduced, which is suspended in water, and the suspension is heated to the boil for about 60 minutes. The nitro compound to be reduced is then introduced through the line 2. The reaction commences immediately. The iron constantly required is then added at intervals of about 20 minutes or continuously through a metering valve mounted at 3. Together with the precipitated iron oxide, the resulting aromatic amine flows continuously through the overflow pipe 4. The iron oxide sludge is filtered off from the overflow solution, washed and dried. It is of excellent quality and particle size and can be used direct as iron oxide pigment. It consists in the main of almost pure $Fe_3O_4$. The amino compound is advantageously precipitated from the filtrate by changing the pH, collected by filtration, washed, and, if desired, dried.

The advantage of the process of this invention also resides in particular in the fact that the amount of iron present in the reaction is not critical and is constantly present in substantial excess, based on the stoichiometric amount of iron required, as only a portion of the total amount of substance to be reduced is continually in reaction.

The reduction proceeds very rapidly according to the process of the invention, so that the concentration of the continuously added nitro compound speedily falls to zero. Stirring with the aim of promoting a subsequent reaction as in the batchwise method is therefore unneccessary.

The iron balance is only of importance in the process of the invention in so far as the requisite amount of iron is to some extent maintained in continuous operation over a longer period of time. A check in this respect can be carried out by constantly weighing the reactor.

The reaction rate increases quite substantially as a result of the large excess of iron constantly present. It is about three times higher and more than in the batchwise operated Béchamp reduction, resulting in a substantially higher space-time and energy yield. A further advantage is that the iron oxide is obtained in pure form with good filtering properties without being contaminated by iron particles.

In contrast to the batchwise operated method, virtually no losses of iron and product occur in the continuous method during the necessary separating operations. In order to utilise the iron or iron oxide by the old method, a three-component separation would be necessary, namely iron, iron oxide, amine. This is now dispensed with entirely and results in a saving of time and material.

As the iron oxide furthermore is obtained as $Fe_3O_4$, the amount of it is substantially smaller. This fact has advantageous consequences for installation, storage and transportation costs both of the iron employed and of the iron oxide obtained.

The occurrence of erosion in the apparatus is slight on account of the use of relatively fine iron particles. Erosion can be reduced still further by the use of suitable stirrers, turbulence inhibitors and other devices built into the reactor.

The amines obtained by the process of the invention are intermediates for many fields of use in the chemical industry. The letter or name acids in particular are used in dyestuff synthesis, for example for the production of azo dyes as diazotisation or coupling components.

The following Examples illustrate the procedure of the continuous reduction method of the invention.

EXAMPLE 1

A 2 liter steel reactor (1), equipped with metering means, iron separator and overflow pipe (4) as illustrated in the attached drawing, is charged with 603 g of water and 750 g of iron powder through inlet (3), and the suspension is heated to about 100° C. Under these conditions the iron is activated for 60 minutes. Then the continuous addition of the nitro solution through pipe (2) as 20% aqueous neutral solution is begun at about 100° C. A total of 7500 g (4 moles) of a mixture of 1-nitronaphthalene-5-sulfonic and 1-nitronaphthalene-8-sulfonic acid (so-called nitro-peri/laurent acid mixture), which additionally contains 2 moles of nitro by-products of the isomers, are employed.

On a laboratory scale (for the sake of simplicity), 50 g of iron powder are added at intervals of 15 minutes until the total amount of iron is 1750 g. The reaction products, consisting of the mixture of 1-naphthylamino-5-sulfonic acid and 1-naphthylamino-8-sulfonic acid, and iron oxide precipitate, are removed continuously from the reaction vessel through the overflow pipe. The reaction on this scale is complete after 4 hours.

The precipitated iron oxide is filtered off from the reaction solution of the continuous overflow and the reactor contents, affording 8357 g of a filtrate containing 1-naphthylamino-5-sulfonic acid and 1-naphthylamino-8-sulfonic acid. The aminosulfonic acids are precipitated by acidifying this solution to a pH value of about 5.4 and 3 respectively, collected by filtration, washed and dried, affording 885 g of product, which corresponds to a virtually quantitative yield. In addition to the product, the reduction vessel residue obtained after the reaction with the above mixture is worked up. After separation of the iron oxide adhering to it, this residue contains 760 g of unreacted iron powder, based on a bath of 4 moles.

Accordingly the consumption of iron is 990 g of iron per 6 moles of the batch, which corresponds to about 165 g of iron per mole of reduced nitro groups.

EXAMPLE 2

The procedure of Example 1 is repeated, except that equivalent amounts of nitro-C acid (2-nitronaphthalene-4,8-disulfonic acid are reduced instead of nitro-peri/laurent acid, affording the corresponding C acid (2-naphthylamino-4,8-disulfonic acid) as product in equally good yield.

EXAMPLE 3

In accordance with Example 1, the corresponding amines are obtained in excellent purity and yield from the nitro compounds listed above under the examples of the preferred nitro compounds.

EXAMPLE 4

The procedure described in Example 1 is repeated, except that equivalent amounts of sodium p-nitroaniline-2-sulfonate are reduced instead of nitro-peri/laurent acid, affording the corresponding 1,4-diaminophenyl-2-sulfonic acid as product in equally good yield.

EXAMPLE 5

The procedure described in Example 1 is repeated using a reaction mixture obtained from preceding processes and which contains, in addition to minor impurities, principally the following main constituents to be reduced:

|  | mol. wt. | kg | % age of the total amount used | kmols |
|---|---|---|---|---|
| 1-nitronaphthalene-5-sulfonic acid | 253.24 | 275.12 | 64.9994 | 1.0864 |
| 1-nitronaphthalene-8-sulfonic acid | 253.24 | 67.03 | 15.863 | 0.2647 |
| 1-nitronaphthalene-4,8-disulfonic acid | 333.30 | 8.10 | 1.913 | 0.0243 |
| 1-nitronaphthalene | 173.17 | 2.18 | 3.516 | 0.0126 |

All the nitro groups of the above compounds are reduced to amino groups. The reaction is in no way adversely affected by the heterogeneous composition and the yield, based on the individual components, is quantitative.

What is claimed is:

1. A process for the reduction of aromatic nitro compounds to amino compounds in the liquid phase using iron as reducing agent, which comprises carrying out the reduction continuously such that the reducing iron, based on the amount of nitro compound present in the reactor, is present in an amount substantially in excess of the stoichiometric amount, and effecting the continuous removal of the reaction products such that the substantial excess of reducing iron is also constantly present in the reactor during the reduction.

2. A process according to claim 1, wherein the nitro compounds to be reduced are introduced into the reaction continuously or in portions.

3. A process according to claim 1, wherein the reduction is carried out in an aqueous reaction medium.

4. A process according to claim 1, wherein the reduction is carried out in a polar solvent.

5. A process according to claim 1, wherein the reduction is carried out at a pH value between 4 and 10.

6. A process according to claim 5, wherein the reduction is carried out at a pH value between 5.5 and 8.5.

7. A process according to claim 1, wherein the reduction is carried out at a temperature between 70° and 130° C.

8. A process according to claim 7, wherein the reduction is carried out at a temperature between 90° and 110° C.

9. A process according to claim 1, wherein the reducing agent is carbon-containing iron.

10. A process according to claim 9, wherein untreated cast-iron turnings are used.

11. A process according to claim 10, wherein the cast-iron turnings have a particle size of up to 0.5 mm.

12. A process according to claim 1, wherein the substances to be reduced are dissolved in the reaction medium.

13. A process according to claim 1, wherein the substances to be reduced are suspended in the reaction medium.

14. A process according to claim 1, wherein nitronaphthalenesulfonic acids are reduced.

15. A process according to claim 14, wherein 1-nitronaphthalene-5-sulfonic acid, 1-nitronaphthalene-8-sulfonic acid or 2-nitronaphthalene-;b 4,8-disulfonic acid are reduced to the corresponding amino acids.

16. A process according to claim 1, wherein nitrostilbenesulfonic acids are reduced.

17. A process according to claim 16, wherein 4,4'-dinitrostilbene-2,2'-disulfonic acid is reduced as aromatic nitro compound.

18. A process according to claim 1, wherein the reaction and the separation of the reaction products consisting of amine and iron oxide are carried out in one and the same reaction vessel.

* * * * *

UNITED STATES PATENT AND TRADEMARK OFFICE
CERTIFICATE OF CORRECTION

PATENT NO. : 4,217,304
DATED : August 12, 1980
INVENTOR(S) : Bernhard Albrecht, et al.

It is certified that error appears in the above-identified patent and that said Letters Patent are hereby corrected as shown below:

Column 6, line 40, delete "; b".

Signed and Sealed this

Twenty-eighth Day of October 1980

[SEAL]

Attest:

SIDNEY A. DIAMOND

Attesting Officer

Commissioner of Patents and Trademarks